United States Patent
Horiba et al.

(10) Patent No.: US 10,276,276 B1
(45) Date of Patent: Apr. 30, 2019

(54) RADIATION PHASE-CONTRAST IMAGE CAPTURING DEVICE

(71) Applicant: Shimadzu Corporation, Kyoto (JP)

(72) Inventors: Akira Horiba, Kyotanabe (JP); Shingo Furui, Kyoto (JP); Koichi Tanabe, Uji (JP); Toshinori Yoshimuta, Takatsuki (JP); Kenji Kimura, Yamatokoriyama (JP); Hiroyuki Kishihara, Kizugawa (JP); Takahiro Doki, Kizugawa (JP); Satoshi Sano, Soraku-gun (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 15/881,329

(22) Filed: Jan. 26, 2018

(51) Int. Cl.
*G21K 1/02* (2006.01)
*G21K 1/10* (2006.01)
*G03B 42/02* (2006.01)
*A61B 6/00* (2006.01)

(52) U.S. Cl.
CPC .............. *G21K 1/025* (2013.01); *G03B 42/02* (2013.01); *G21K 1/10* (2013.01); *A61B 6/484* (2013.01); *G21K 2207/005* (2013.01)

(58) Field of Classification Search
CPC ............ G21K 1/025; G21K 1/10; G03B 42/02
See application file for complete search history.

(56) References Cited

U.S. PATENT DOCUMENTS

| 2012/0020454 | A1  | 1/2012 | Murakoshi |             |
|--------------|-----|--------|-----------|-------------|
| 2012/0140883 | A1* | 6/2012 | Iwakiri   | A61B 6/4233 |
|              |     |        |           | 378/62      |
| 2014/0177789 | A1* | 6/2014 | Baturin   | A61B 6/484  |
|              |     |        |           | 378/35      |
| 2018/0177475 | A1* | 6/2018 | Koehler   | A61B 6/4035 |

FOREIGN PATENT DOCUMENTS

JP          2012-024339         2/2012

* cited by examiner

*Primary Examiner* — Hugh Maupin
(74) *Attorney, Agent, or Firm* — Muir Patent Law, PLLC (57) ABSTRACT

A movable collimator is realized with a simple mechanism in a radiation phase-contrast image capturing device. A collimator is integrated with a multi-slit or a phase grating to provide a simpler device configuration. In some examples, the collimator and the multi-slit or phase grating may be configured to move while still providing image capturing.

20 Claims, 10 Drawing Sheets

Movable unit

Movable unit

FIG. 9

Absorption grating

FIG. 10

Movable unit

RADIATION PHASE-CONTRAST IMAGE CAPTURING DEVICE

TECHNICAL FIELD

The present disclosure relates to a radiation phase-contrast image capturing device for imaging an internal structure of an object using phase-contrast of radiation transmitted through an object, and more particularly to a radiation phase-contrast image capturing device of a type performing scanning image capturing.

BACKGROUND ART

Conventionally, as a radiation image capturing device for imaging an internal structure of an object by making radiation transmit through the object, various devices have been proposed. A commonly-used radiation image capturing device is configured to capture a radiation projection image by irradiating an object with radiation to make the radiation transmit through the object. In such a projection image, shading appears depending on the ease of permeation of radiation, which represents the internal structure of the object.

With such a radiation image capturing device, it only can capture an image of an object having properties capable of absorbing radiation to some extent. For example, soft biological tissues hardly absorb radiation. Even if it is tried to capture an image of such a tissue with a general device, nothing is reflected on the projection image. When trying to capture an image of an internal structure of an object that does not absorb radiation as described above, there is a theoretical limit in a general radiation image capturing device.

Under the circumstances, a radiation phase-contrast image capturing device for imaging an internal structure of an object by utilizing a phase-contrast of transmitted radiation has been proposed. Such a device is configured to image an internal structure of an object by utilizing Talbot interference.

Figure 17:
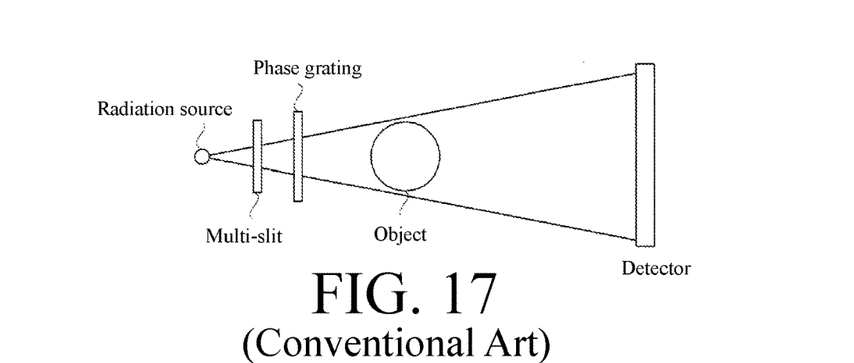
FIG. 17 is a schematic diagram illustrating a configuration of a radiation phase-contrast image capturing device of a conventional configuration.

FIG. 17 illustrates a radiation phase-contrast image capturing device. The radiation phase-contrast image capturing device is provided with a radiation source configured to irradiate radiation, a multi-slit configured to align phases of the radiation, a phase grating with a pattern of a streak form, and a detector configured to detect radiation. In the device of FIG. 17, an object may be positioned in between the phase grating and the detector. The multi-slit is configured such that vertically extended slits are arranged in a lateral direction. The phase grating is configured such that vertically extended shielding lines which are less likely to transmit radiation are arranged in a lateral direction.

The principle of a radiation phase-contrast image capturing device will be briefly explained. When phase-matched radiation is irradiated to the phase grating, a self-image of the phase grating appears at a position away from the phase grating by a specific distance (Talbot distance). The detector is adjusted in position with respect to the phase grating so that the self-image is reflected. This self-image looks like an image in which a shadow of the phase grating is projected. However, it should be noted that the self-image is not a simple projection but results from an interference fringe caused by radiation interference.

When an object is placed between a phase grating and a detector, the radiation emitted the phase grating will transmit through the object before being detected by the detector. The self-image appearing on the detector at this time is slightly disturbed by transmitting through the object. This disturbance is due to the phase shift caused while the radiation transmits through the object.

By detecting the distorted self-image with the detector and subjecting the self-image to predetermined image processing, an image showing the phase-contrast distribution of the radiation transmitted through the object can be generated. Such an image is referred to as a transparent image. According to the radiation phase-contrast image capturing device, a transparent image representing the internal structure of the object can be generated even for objects that do not absorb radiation.

A detector used for a radiation phase-contrast image capturing device is expensive. This is because the self-image has a very fine in pattern and therefore the detection elements of the detector are required to be miniaturized in order to capture the self-image. The self-image has a stripe pattern composed of regularly arranged dark lines, but the arrangement pitch of the dark lines cannot be freely changed. The self-image is an image caused by interference of light. Therefore, the arrangement pitch of shielding lines arranged in a phase grating is determined by the wavelength of radiation. Considering the necessity to make radiation transmit through the object, it is necessary to set the wavelength of radiation to be considerably short, and the arrangement pitch of shielding lines in the phase grating becomes small correspondingly. Therefore, the arrangement pitch of the dark lines of the self-image becomes narrow. In order to detect such a fine image, a detector higher in the spatial resolution is required. Such a detector is expensive.

Figure 18:
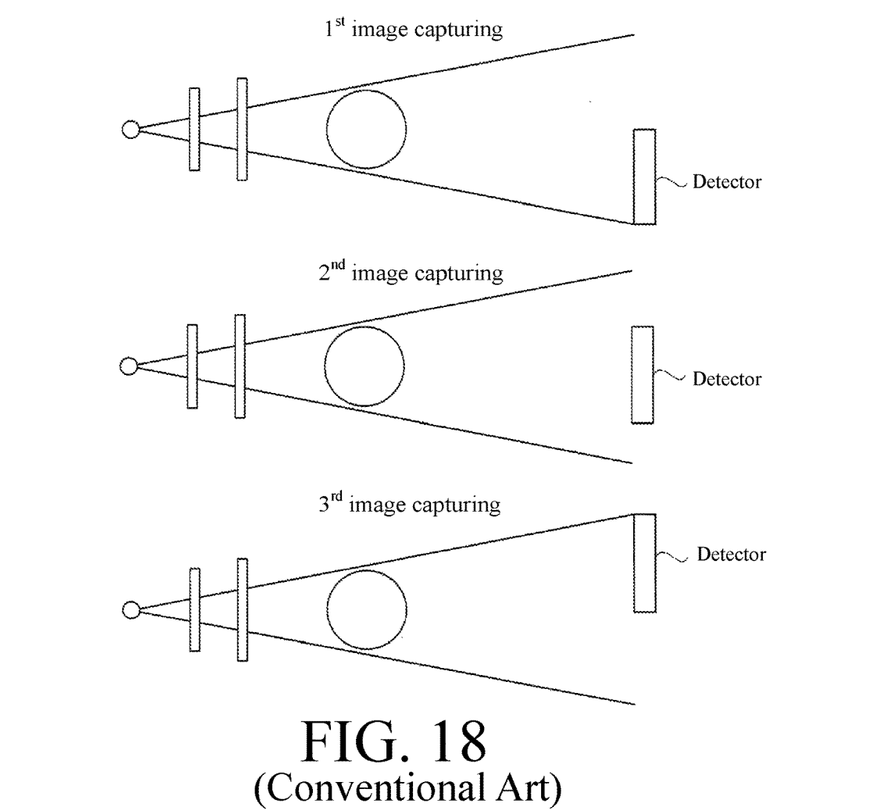
FIG. 18 is a schematic diagram illustrating a configuration of a radiation phase-contrast image capturing device having a conventional configuration.

Under the circumstances, in order to make the detector less expensive, devices that perform scanning image capturing have been proposed. That is, as shown in FIG. 18, a self-image of an object may be obtained by performing image capturing a plurality of times while moving the detector with respect to the object. In FIG. 18, the detector is too small to capture the entire image of the object in the image capturing visual field in one image capturing. However, if one self-image is obtained by performing image capturing, for example, three times while moving the detector and combining three pieces of the self-image obtained at this time, even if the size of the detector is reduced, a self-image of the absorption grating covering the entire object can be obtained. If the size of the detector is small, the production cost of the device can be suppressed accordingly.

Figure 19:
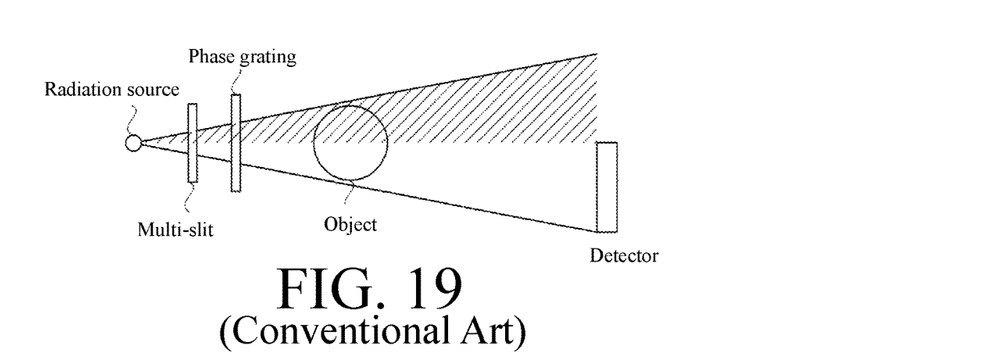
FIG. 19 is a schematic diagram illustrating a configuration of a radiation phase-contrast image capturing device having a conventional configuration.

However, with the configuration as shown in FIG. 18, unnecessary exposure to the object occurs. The spread of radiation output from the radiation source is wide so that the radiation is able to reach the entire area of the object. However, as shown in FIG. 18, in the case of scanning image capturing, it is impossible to perform image capturing of the entire area of the object at one time, so the image capturing is performed three times separately. For example, in the case of the $1^{st}$ image capturing, as shown in FIG. 19, the radiation necessary for capturing the self-image is only a part of the radiation which spreads from the radiation source downward in the figure and is incident on the detector. The other part of the radiation which spreads from the radiation source upward and is shown with hatched lines in FIG. 19 will not be detected with the detector. Therefore, the radiation indicated with the hatched lines is the so-called useless radiation irradiated to the object even though it does not contribute to the image capturing. In cases where the object has physical properties which deteriorate due to radiation irradiation or in cases where the object is an organism, such unnecessary radiation irradiation should be avoided.

In order to avoid that the object is irradiated with unnecessary radiation during the scanning image capturing, it is only necessary to provide a collimator that absorbs radiation (see, for example, Japanese Unexamined Patent Application Publication No. 2012-24339, hereby incorporated by reference).

Even in the case of not performing scanning image capturing, there is a case in which it is better to provide a collimator. There is a case in which it is desirable to provide a mode for capturing an image of only a part of the object. In such cases, it is better to provide a collimator so that the part not related to the image capturing is not irradiated with radiation.

SUMMARY OF THE INVENTION

However, the configuration of the aforementioned device to which a collimator is to be provided becomes complicated.

Figure 20:
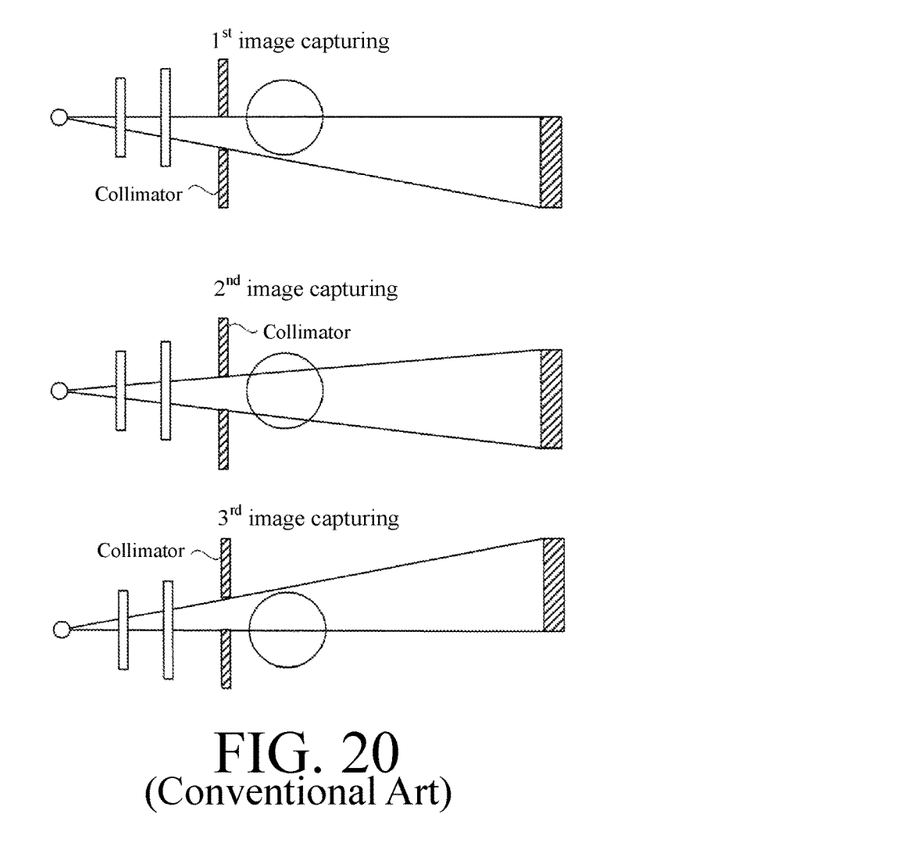
FIG. 20 is a schematic diagram illustrating problems of a radiation phase-contrast image capturing device having a conventional configuration.

FIG. 20 illustrates problems occurring when a collimator is provided in a conventional device. In the case of the scanning image capturing, continuous image capturing is performed while moving the detector relative to the object, but the path of the radiation beam required for the image capturing differs in each image capturing. That is, in the $1^{st}$ image capturing, the radiation must be irradiated so as to transmit through the lower side of the object, and in the $2^{nd}$ image capturing, the radiation must be irradiated so as to transmit through the center of the object. Then, in the $3^{rd}$ image capturing, the radiation must be irradiated so as to transmit through the upper side of the object.

As will be apparent, a mechanism for moving the collimator in coordination with the detector is required. In FIGS. 17 to 20, it looks that there exists a wide space between the phase grating and the detector and therefore it is easy to newly provide a movable collimator. In reality, however, it is quite difficult to provide a movable collimator. This is because each figure is depicted such that there is a considerable spacing between the phase grating and the detector, but this is for purposes of illustration. In an actual device, the phase grating and the detector are not necessarily spaced apart from each other as illustrated. Further, the positional relationship of the radiation source, the multi-slit, the phase grating, and the detector have strict requirements. Without making these structural members in a predetermined positional relationship, the self-image of the phase grating will not be generated on the detector. In such a situation in which there is a positional constraint, it is quite difficult to provide a movable collimator.

Even in the case of not performing scanning image capturing but performing image capturing of only a part of an object, the same problem occurs. In other words, in the case of attempting to perform image capturing by irradiating a part of an object with radiation, there is a case in which it is desired to limit the spread of radiation. In order to realize this limitation, it is also necessary to provide a collimator in the device. This collimator is required to be movable because the image capturing range of the object cannot be changed if the collimator is fixed. However, it is quite difficult to provide a movable collimator in the device as described above.

The present invention was made in view of the aforementioned circumstances, and the purpose is to realize a movable collimator by a simple mechanism in a radiation phase-contrast image capturing device.

As disclosed herein, a radiation phase-contrast image capturing device according to embodiments of the present invention may include (A) a radiation source configured to irradiate radiation, (B) a unit configured by integrally superimposing a multi-slit that aligns phases of radiation generated from the radiation source by making the radiation transmit through and a collimator that limits spread of the radiation, (C) a phase grating in which absorbers absorbing radiation and extending in a longitudinal direction are arranged in a lateral direction and Talbot interference occurs when radiation is transmitted therethrough, (D) a detector configured to detect a self-image of the phase grating, wherein the radiation source, the unit, the phase grating, and the detector are arranged in this order, and (E) a unit moving mechanism configured to change a position where radiation collimated with the unit is incident on the object is changed by moving the unit in a direction orthogonal to an irradiation direction of the radiation with respect to an object positioned between the unit and the detector.

Accordingly, a movable collimator can be provided in a radiation phase-contrast image capturing device by merely providing a simple mechanism such that the collimator and the multi-slit are integrated. Therefore, when the collimator is moved, the multi-slit is also moved accordingly.

Conventional radiation phase-contrast image capturing devices have a configuration such that the multi-slit of a conventional configuration is fixed in a device. In contrast, according to the configuration of the disclosed embodiments, the device configuration becomes much simpler than a structure in which a collimator is provided in a device independently of a multi-slit. On the other hand, even if it is configured such that the multi-slit is moved, there is no problem in the image capturing.

Further, in the aforementioned radiation phase-contrast image capturing device described above, it is more preferable that the radiation source be integrated with the unit and the unit moving mechanism integrally be configured to integrally move the multi-slit, the collimator, and the radiation source.

According to the configuration of some embodiments, the positional relationship between the radiation source and the collimator may be maintained. When the collimator is moved with respect to the object, the radiation source may also be moved together with the collimator. In some examples, radiation is always irradiated from a direction orthogonal to the collimator regardless of the movement of the collimator. In this way, it is possible to always perform image capturing of the object with a strong dose.

In some examples, the radiation phase-contrast image capturing device includes (A) a radiation source configured to irradiate radiation, (C1) a unit configured by integrally superimposing a phase grating in which absorbers absorbing radiation and extending in a longitudinal direction are arranged in a lateral direction and Talbot interference occurs when radiation is transmitted therethrough and a collimator that limits spread of the radiation, (D) a detector configured to detect a self-image of the phase grating, wherein the radiation source, the unit, the detector are arranged in this order, and (E) a unit moving mechanism configured to change a position where radiation collimated with the unit is incident on the object is changed by moving the unit in a direction orthogonal to an irradiation direction of the radiation with respect to an object positioned between the unit and the detector.

In some examples, the phase grating and the collimator are integrated. Therefore, when the collimator is moved, the phase grating is also moved accordingly. Accordingly, the device configuration becomes much simpler than a structure in which a collimator is provided in a device independently of a phase grating, and there is no problem in the image capturing.

Further, a multi-slit may be configured to align phases of radiation generated from the radiation source and may be arranged between the radiation source and the unit. Even in cases where a collimator and a phase grating are integrated, it is possible to adopt a device configuration equipped with a multi-slit.

Further, it may be preferable to include a detector moving mechanism configured to move the detector in a direction orthogonal to an irradiation direction of radiation in synchronization with a movement of the unit, and an image combining unit configured to combine a plurality of images obtained by continuous image capturing while moving the unit and the detector to generate a single image.

As noted, when the detector is moveable, the detector can be made small. This is because a self-image of the phase grating can be image captured in a wider range by performing scanning image capturing.

In some examples, it may be preferable that an absorption grating in which absorbers absorbing radiation and extending in a longitudinal direction be arranged in a lateral direction is provided so as to cover a radiation incident surface of the detector. When the absorption grating is provided so as to cover the radiation incident surface of the detector, it is possible to perform imaging of the self-image of the phase grating even if the spatial resolution of the detector is low.

In some examples, a movable collimator can be provided in the radiation phase-contrast image capturing device with a simple mechanism. Conventionally, a multi-slit of a conventional configuration is fixed in a device. According to the configuration of the present invention, the device configuration becomes much simpler than a structure in which a collimator is provided in the device independently of a multi-slit with no problem in the image capturing.

EMBODIMENTS FOR CARRYING OUT THE INVENTION

Hereinafter, embodiments for carrying out the present invention will be described with reference to drawings. The embodiments are described, and illustrated in the drawings, in terms of functional blocks or units. These blocks/units may be physically implemented by electronic (or optical) circuits such as logic circuits, discrete components, microprocessors, hard-wired circuits, memory elements, wiring connections, and the like, which may be formed together in a single integrated circuit (e.g., as a single semiconductor chip) or as separate integrated circuits and/or discrete components (e.g., several semiconductor chips wired together on a printed circuit board). These blocks/units may be implemented by a processor (e.g., a microprocessor, a controller, a CPU, a GPU) or processors that are programmed using software to perform various functions discussed herein. Each block/unit and/or module may be implemented by dedicated hardware, or as a combination of dedicated hardware to perform some functions and a processor to perform other functions. Also, each block/unit of the embodiments may be embodied by physically separate circuits and need not be formed as a single integrated circuit or a single processor. Note that "X-ray" corresponds to radiation according to the embodiments, and "FPD" is an abbreviation of a flat panel detector.

Example 1

Figure 1:
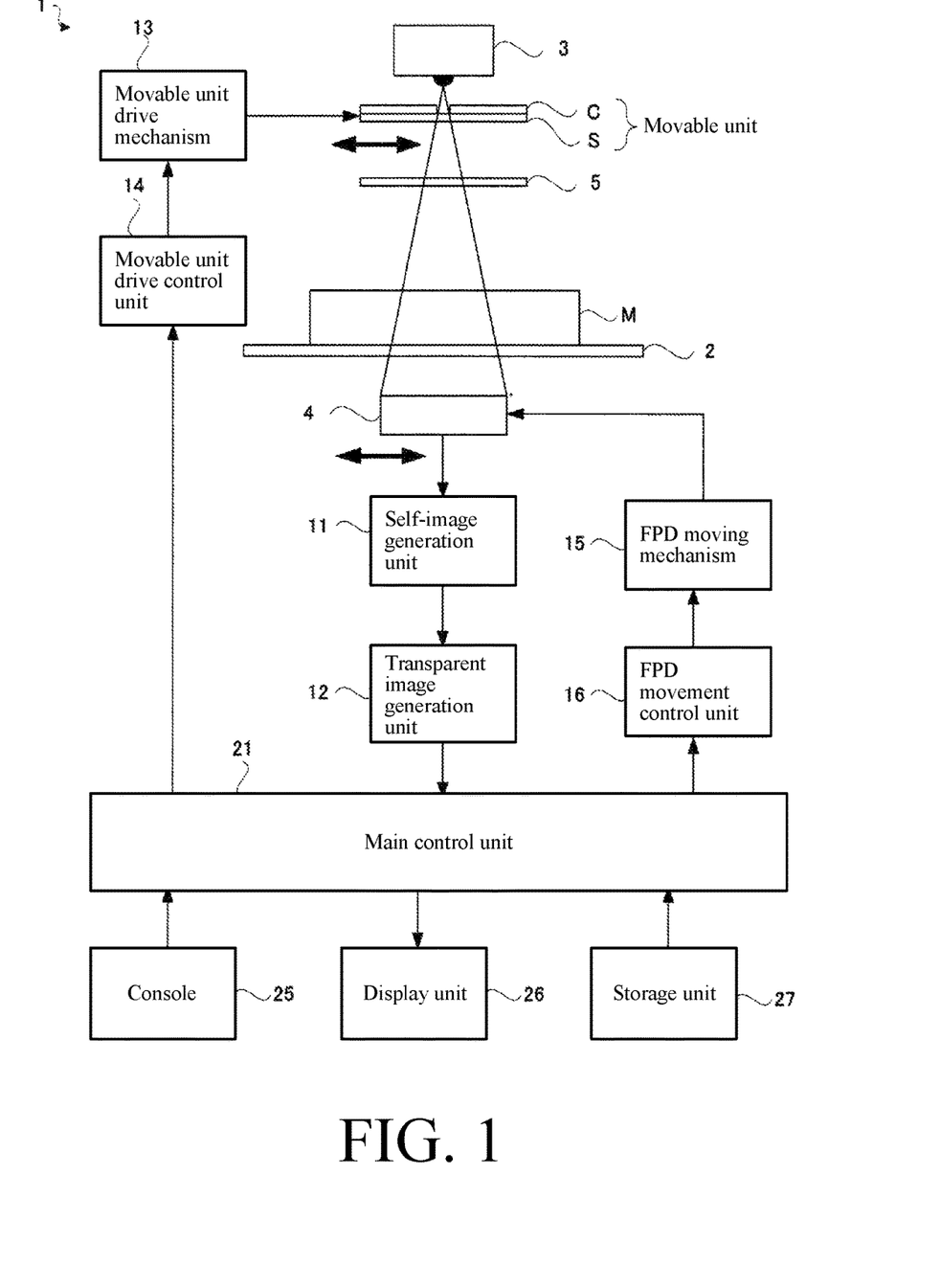
FIG. 1 is a functional block diagram illustrating the overall configuration of an X-ray phase-contrast image capturing device according to Example 1.

FIG. 1 shows the overall configuration of an X-ray phase-contrast image capturing device 1 according to an embodiment of the present invention. As shown in FIG. 1, the configuration of the X-ray phase-contrast image capturing device is equipped with a platform 2 on which an object M is to be placed, an X-ray source 3 for irradiating an X-ray towards the platform 2, and an FPD 4 for detecting the X-ray that have transmitted through the platform 2. The X-ray source 3 irradiates an X-ray toward the lower side of the paper surface of FIG. 1. The X-ray irradiated at this time is a beam having a spread to some extent. The FPD 4 is equipped with a detection surface for detecting an X-ray. The FPD 4 has an elongated shape. The paper surface penetration direction in FIG. 1 corresponds to a longitudinal direction of the FPD 4 (the long side of FPD 4), and the paper surface right-left direction corresponds to a short side direction of the FPD 4. For example, the upper surface of the FPD 4 may be configured to receive and detect X-rays irradiated thereon that are transmitted through phase grating 5. The upper surface FPD 4 may have a rectangular shape, having a long side extending in a direction perpendicular to the paper surface of FIG. 1 and having a short side extending in the right-left direction of FIG. 1. The FPD 4 detects a self-image of the phase grating 5 which will be described later. The FPD 4 corresponds to the detector described herein.

Various parts related to Talbot interference are attached between the X-ray source 3 and the platform 2. In the vicinity of the X-ray source 3, a multi-slit S for aligning the phases of the X-ray is provided. This multi-slit S is made of material that does not allow an X-ray to transmit through, and through-holes elongated in the longitudinal direction are arranged in the lateral direction. Therefore, a part of the X-ray incident on the multi-slit S can transmit through the multi-slit S through the through-holes. When an X-ray is transmitted through the multi-slit S, the phases of the X-ray which were not aligned are aligned, which enhances the coherency of the X-ray. The multi-slit S is configured to align the phases of the X-ray generated from the X-ray source 3 that are transmitted therethrough.

Between the X-ray source 3 and the platform 2, the phase grating 5 is provided separately from the multi-slit S. This phase grating 5 is configured such that linear absorbers extend in the lateral direction of the FPD 4 (extending in the short side direction of the FPD 4) and are arranged in the longitudinal direction of the FPD 4. Each absorber has properties of absorbing an X-ray (e.g., is opaque to X-rays emitted from the X-ray source 3). Therefore, when an X-ray is projected onto the phase grating 5, the X-rays incident on the absorber are absorbed there, and the X-rays incident between two adjacent absorbers are transmitted therethrough. To the FPD 4, a self-image representing five patterns of the phase grating 5 is projected. It should be noted that this self-image is not just a projection image of the phase grating 5. The self-image is an interference fringe generated on the FPD 4 due to the X-ray interference caused by the phase grating 5. The self-image is detected by the FPD 4. The direction in which the absorber extends corresponds to the right-left direction of the paper surface of FIG. 1. The phase grating 5 is configured such that absorbers absorbing an X-ray and extending in the lateral direction of FPD 4 and are arranged side-by-side in the lateral direction of FPD 4, the phase grating generates Talbot interference when the radiation is transmitted therethrough.

The self-image image generation unit 11 generates a self-image imaging the self-image of the phase grating 5 based on the X-ray detection data outputted by the FPD 4. The self-image reflects the stripe pattern of the phase grating 5. This self-image is sent to the transparent image generation unit 12. The transparent image generation unit 12 generates a transparent image imaging the phase shift of the X-ray by interpreting the disturbance of the stripe pattern on the self-image. The transparent image visualizes the deviation of the phase of the X-ray which differs depending on the location of the object M, and shows the internal structure of the object M. The self-image image generation unit 11 generates a single image by combining a plurality of images obtained by successive image capturing while moving the multi-slit S (movable unit C, S which will be described later) and the FPD 4. The self-image image generation unit 11 corresponds to the image combining unit described herein.

The X-ray source 3, the multi-slit S (movable unit C, S which will be described later), the phase grating 5, the platform 2, and the FPD 4 are arranged in this order. In the case of FIG. 1, the platform 2 is provided between the phase grating 5 and the FPD 4, but the platform 2 may be provided between the multi-slit S and the phase grating 5. In any case, the positional relationship of the X-ray source 3, the multi-slit S, the phase grating 5, and the FPD 4 is relatively strictly determined. This is because these parts must satisfy a predetermined positional relationship in order to generate the self-image of the phase grating 5 on the detection surface of the FPD 4.

The collimator C is made of material that does not allow an X-ray to transmit through, and has an elongated window. X-rays may be transmitted through the collimator C through this window. Although it may be considered such that the collimator C has a configuration similar to that of the multi-slit S, there are the following differences. The multi-slit S has a plurality of through-holes arranged. On the other hand, the collimator C has only one window. Further, each through-hole (e.g., each slit) of the multi-slit S has a width of several μm. On the other hand, the lateral width (the width in a direction orthogonal to the longitudinal direction, shorter than the length in the longitudinal direction) of the window of the collimator C is large, such as about several mm to several tens mm, such as between 3 mm to 50 mm (e.g., greater than 1000 times the width of the slits of each through-hole of the multi-slit S). The window of the collimator C corresponds to the shape of the FPD 4 (e.g., having a rectangular shape which may be geometrically similar to a rectangular shape of the upper surface of the FPD 4). The paper surface penetration direction in FIG. 1 corresponds to the longitudinal direction of the window (long side of the window, such as the long side of a rectangle for a rectangularly shaped window), and the paper surface right-left direction corresponds to the short side of the window (such as the short side of a rectangle). The collimator C is configured to limit the X-ray so that unnecessary X-ray which is not necessary for irradiating the whole detection surface of the FPD 4 among the X-ray irradiated from the X-ray source 3 is not directed to the object M.

In this example, the collimator C and the multi-slit S are superimposed one on the other (adhered together) to form an integral movable unit C, S. When the collimator C is moved, the multi-slit S is also moved accordingly, so that the positional relationship thereof does not change. The movement of the collimator C is realized by the movable unit drive mechanism 13 (e.g. a servomotor). With this mechanism, the collimator C can be moved in the right-left direction of the paper surface of FIG. 1. The movable unit drive control unit 14 is configured to control the movable unit drive mechanism 13. The movable unit drive mechanism 13 is configured to move the movable unit C, S in a direction orthogonal to the irradiation direction of the X-ray with respect to the object M positioned between the movable unit C, S and the FPD 4. With this, the position where the X-ray collimated by the movable unit C, S is incident on the object M is changed. The movable unit drive mechanism 13 corresponds to the unit moving mechanism described herein.

The FPD 4 can also be moved. The movement of the FPD 4 is realized by the FPD moving mechanism 15. With this mechanism, the FPD 4 can be moved in the right-left direction of the paper surface of FIG. 1. The FPD movement control unit 16 is configured to control the FPD moving mechanism 15. The FPD moving mechanism 15 may be configured to move the FPD 4 in a direction orthogonal to the irradiation direction of the X-ray in synchronization with the movement of the movable unit C, S. The FPD moving mechanism 15 corresponds to the detector moving mechanism described herein.

The main control unit 21 is configured by a CPU, and executes a program realizing each of the unit 11, 12, 14, and 16. Each of the units 11, 12, 14, and 16 may be realized by an arithmetic unit in charge of each. The console 25 is configured to input an instruction of an operator, and the display unit 26 is configured to display a transparent image. The storage unit 27 stores all the parameters related to the control of the device.

The FPD 4 may have an elongated shape in order to suppress the cost. Therefore, only a narrow range of an object M can be image-captured at once. Therefore, the device may be configured to perform image capturing of the entire area of an object by repeatedly performing the image capturing a plurality of times while moving the FPD 4. Such an image capturing method is called scanning image capturing.

Figure 2:
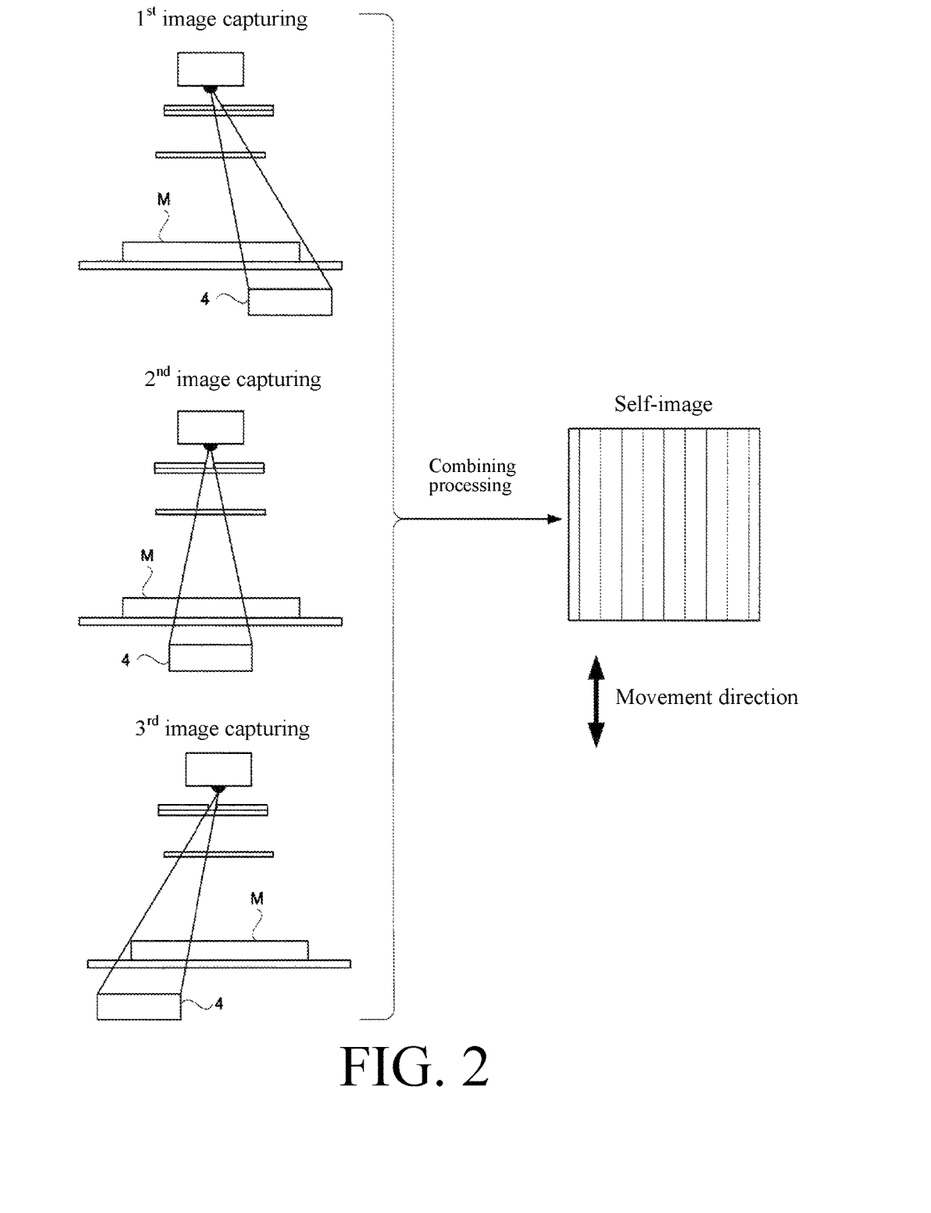
FIG. 2 is a schematic view illustrating scanning image capturing according to Example 1.

FIG. 2 illustrates scanning image capturing according to one example of the present invention. In the example shown in FIG. 2, image capturing of the object M is performed three times. In the $1^{st}$ image capturing, the FPD 4 is positioned on the right side of the object M. At this time, the image capturing is performed on the right side of the object M. In the $2^{nd}$ image capturing, the FPD 4 is positioned on the center of the object M. At this time, the image capturing is performed on the center of the object M. In the $3^{rd}$ image capturing, the FPD 4 is positioned on the left side of the object M. At this time, the image capturing is performed on the left side of the object M. By aligning and combining together these three image fragments obtained by the $1^{st}$, $2^{nd}$, and $3^{rd}$ image capturing, it is possible to obtain a self-image for the entire area of the object M. This combining is performed by the self-image image generation unit 11.

The self-image of the phase grating 5 is present in the self-image generated by the combining processing, but the self-image may be distorted due to the influence of the object M in some places. While the X-ray transmits through the object M, there causes a difference in the phase of the X-ray, and this difference appears as a disturbance of the self-image. Since the self-image represents the disturbance of the self-image corresponding to the entire area of the object, it is possible to generate a transparent image of the entire area of the object from this self-image. By the way, the extending direction of the dark lines appearing in the self-image corresponds to the movement direction of the FPD 4. This is due to the fact that the extending direction of the absorber of the phase grating 5 coincides with the movement direction of the FPD 4.

Figure 3:
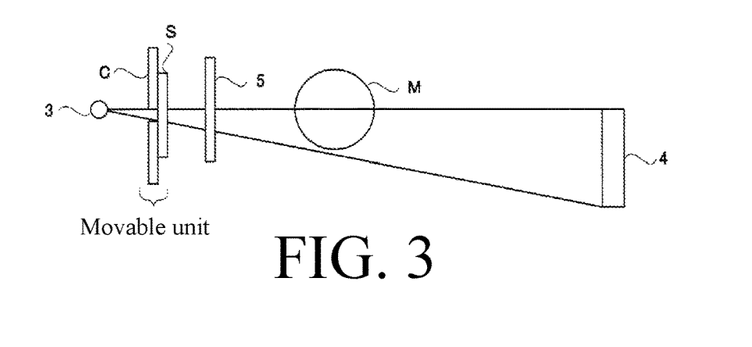
FIG. 3 is a schematic diagram illustrating the positional relationship of each of parts configuring the device of Example 1.

Since the device is provided with the collimator C, unnecessary exposure to the object M can be suppressed. FIG. 3 illustrates this point. The collimator C is provided in front of the multi-slit S as seen from the X-ray source 3 and is configured to transmit an X-ray incident on the detection surface of the FPD 4 through the window and absorb the other X-rays. However, during the scanning image capturing, the FPD 4 moves relative to the object M, so the detection surface of the FPD 4 is moved as well.

Figure 4:
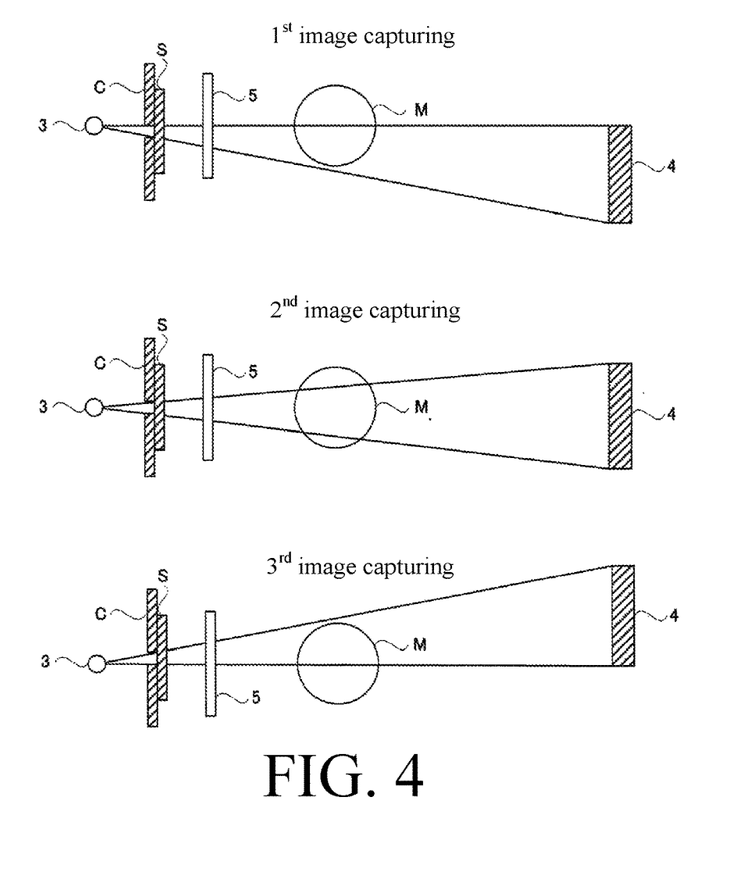
FIG. 4 is a schematic view illustrating the movement of each of parts at the time of the scanning image capturing according to Example 1.

Therefore, in the device according to the present invention, it is configured to move the movable unit C, S during the scanning image capturing. FIG. 4 illustrates the positional relationship of each of parts during the scanning image capturing, and the movable unit C, S composed of the collimator C and the multi-slit S and the FPD 4 highlighted with hatched lines move during the scanning image capturing. On the other hand, the X-ray source 3, the phase grating 5, and the object M, which are not emphasized with hatched lines, do not move during the scanning image capturing.

The upper part in FIG. 4 illustrates the $1^{st}$ image capturing in a series of scanning image capturing. Since the movable unit C, S is located on the lower side of the paper surface of FIG. 4 with respect to the X-ray source 3, the X-ray beam emitting from the movable unit C, S is biased downward. This X-ray beam transmits through the lower portion of the object M, and all of the X-ray beams are incident on the FPD 4 located on the lower side of the X-ray source 3 and detected there.

The middle part in FIG. 4 illustrates the $2^{nd}$ image capturing in a series of scanning image capturing. Since the movable unit C, S is located at the same height as the X-ray source 3, the X-ray beam emitting from the movable unit C, S has no bias. This X-ray beam transmits through the middle portion of the object M, and all of the X-ray beams are incident on the FPD 4 located on the same height as the X-ray source 3 and detected there.

The lower part in FIG. 4 illustrates the $3^{rd}$ image capturing in a series of scanning image capturing. Since the movable unit C, S is located on the upper side of the paper surface of FIG. 4 with respect to the X-ray source 3, the X-ray beam emitting from the movable unit C, S is biased upward. This X-ray beam transmits through the upper portion of the object M, and all of the X-ray beams are incident on the FPD 4 located on the upper side of the X-ray source 3 and detected there.

In this way, the movable unit C, S moves so as to escape from the FPD 4 which is about to surpass. After being passed by the FPD 4, the movable unit C, S moves so as to pursue the FPD 4. In either case of the image capturing, the movable unit allows the X-ray incident on the detection surface of the FPD 4 to transmit therethrough, and absorbs the other X-ray. Although the movable unit C, S and the FPD 4 during the scanning image capturing move in the same direction, the moving distances are different from each other. In the scanning image capturing, the FPD 4 far from the X-ray source 3 moves more than the movable unit C, S close to the X-ray source 3. This is due to the fact that the X-ray beam spreads radially.

As described above, according to the present invention, the movable collimator C can be provided in an X-ray phase-contrast image capturing device by merely providing a simple mechanism. That is, according to the present invention, it is configured such that the collimator C and the multi-slit S are integrated. Therefore, when moving the collimator C of the present invention, the multi-slit S also moves accordingly.

According to a conventional common general technical knowledge, it is configured such that a multi-slit S of a conventional configuration is fixed in a device. This is because the need to move a multi-slit S was not found. The inventors of the present invention have conceived a configuration to integrate the collimator C and the multi-slit S. According to the configuration of the present invention, the device configuration becomes much simpler than a structure in which a collimator C is provided in a device independently of a multi-slit S. On the other hand, even if it is configured such that the multi-slit S is moved, there is no problem in the image capturing. Since the multi-slit S is configured so that the same pattern is arranged in a repeated manner, there is no problem even if scanning image capturing is executed by using the same portion of the multi-slit S.

The present invention is not limited to the aforementioned configurations, and may be modified as follows.

Figure 5:
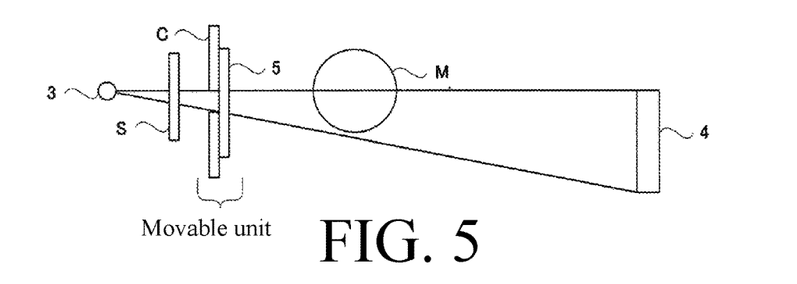
FIG. 5 is a schematic diagram illustrating the positional relationship of each of parts configuring the device according to a modified example of the present invention.

(1) According to the aforementioned configuration, although the collimator C and the multi-slit S may be integrated, the present invention is not limited to this configuration. As shown in FIG. 5, the movable unit C, 5 may be configured by integrating the collimator C and the phase grating 5 in an overlapped (laminated) manner. In this case, it is not necessary to provide a collimator in the multi-slit S.

Figure 6:
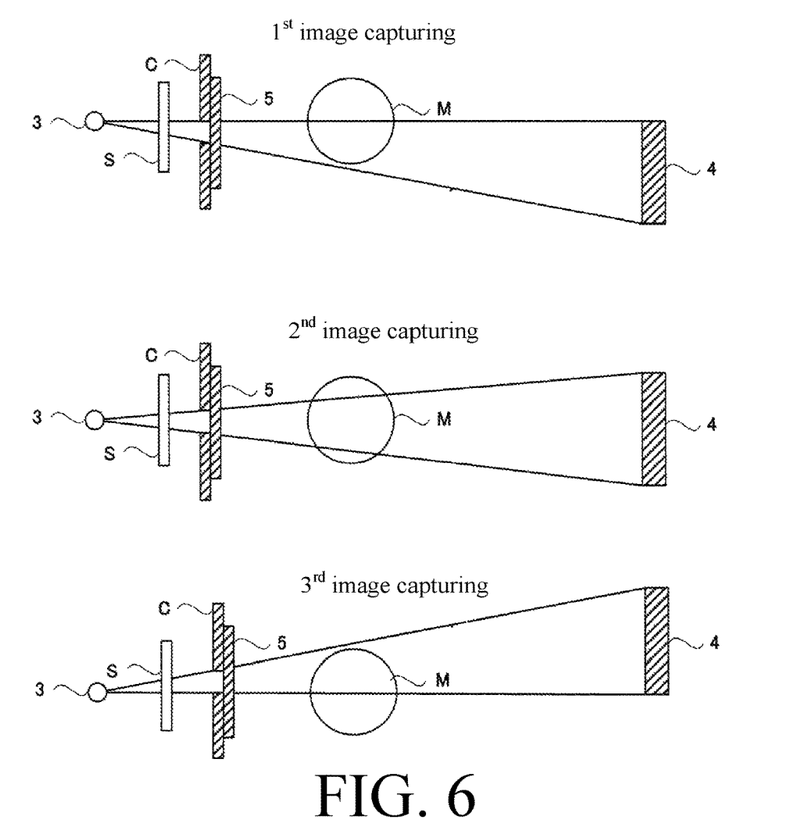
FIG. 6 is a schematic view illustrating the movement of each of parts at the time of performing the scanning image capturing according to a modified example of the present invention.

FIG. 6 illustrates the positional relationship of each of parts during the scanning image capturing according to this modified example. The movable unit C, 5 and the FPD 4 composed of the collimator C, the phase grating 5, and the FPD 4, which are emphasized with hatched lines, move during the scanning image capturing. On the other hand, the X-ray source 3, the multi-slit S, and the object M, which are not emphasized with hatched lines, do not move during the scanning image capturing.

As shown in the upper, middle, and lower parts in FIG. 6, the manner in which image capturing is performed while biasing the direction of the X-ray beam by moving the movable unit C, 5 is the same as in Example 1 explained with reference to FIG. 4.

As shown in FIG. 6, the movable unit C, 5 moves so as to escape from the FPD 4 which is about to surpass. After being passed by the FPD 4, the movable unit C, 5 moves so as to pursue the FPD 4. In either case of the image capturing, the movable unit allows the X-ray incident on the detection surface of the FPD 4 to transmit therethrough, and absorbs the other X-ray. Although the movable unit C, 5 and the FPD 4 during the scanning image capturing move in the same direction, the moving distances are different from each other in the same manner as in Example 1 explained with reference to FIG. 4.

Figure 7:
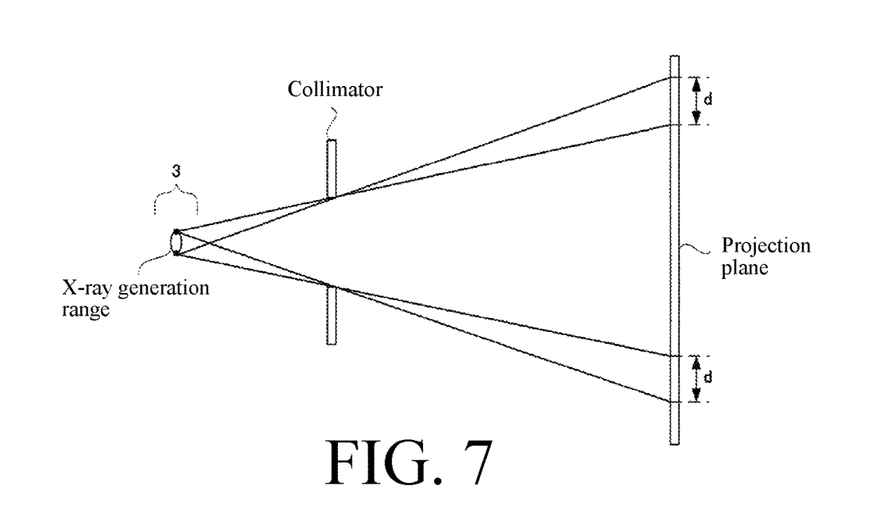
FIG. 7 is a schematic diagram illustrating advantages possessed by the first modified example of the present invention.
Figure 8:
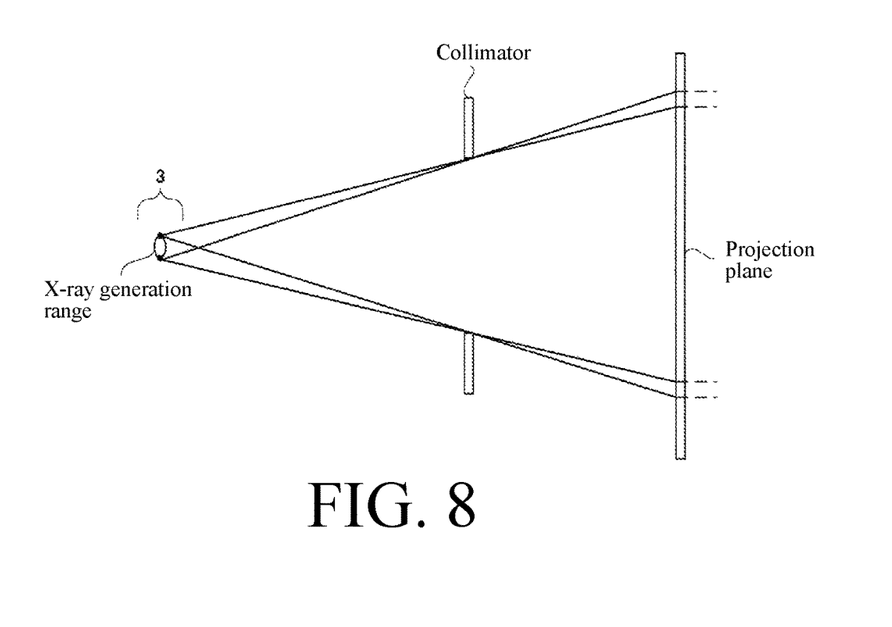
FIG. 8 is a schematic diagram illustrating advantages possessed by a modified example of the present invention.

Providing the collimator C to the phase grating 5 as described above has the following advantages. In reality, a clear transparent image can be obtained when the collimator C is placed on the FPD 4 side as far as possible. FIG. 7 and FIG. 8 explain the reason. FIG. 7 illustrates the state in which the X-ray irradiated from the X-ray source 3 is limited by a collimator and then projected onto a certain projection plane.

Although the X-ray source 3 generates an X-ray from a certain focal point, even if it calls a focal "point", it actually has a certain spread. That is, as shown in FIG. 7, the X-ray source 3 generates an X-ray from the entire X-ray generation range having a certain area. When trying to obtain a transparent image, it is ideal that an X-ray is emitted from one point. However, in reality, it is not as ideal as shown in FIG. 7.

FIG. 7 illustrates a case in which the collimator C is placed close to the X-ray source 3. It will be compared how an X-ray generated at one end of the X-ray occurrence range and an X-ray generated at the other end thereof transmit through the collimator and will be projected on a projection plane. It is understood that the path along which the X-ray generated at one end of the X-ray generation range goes toward the projection plane and the path along which the X-ray generated at the other end of the X-ray generation range goes toward the projection plane are greatly different from each other.

In the case of FIG. 7, when observing the shadow of the collimator where the projection plane is projected, the part corresponding to the window frame is not clear. In the area indicated by the symbol "d" in the projection plane, there occurs a phenomenon in which the X-ray generated at one end of the X-ray occurrence range is incident on without being hindered by the collimator, but the X-ray generated at the other end is not incident on by being blocked by the collimator. Therefore, the area indicated by "d" is a gray zone which is not clear whether or not it is a shadow of the collimator. A configuration in which such a gray zone is projected is undesirable for obtaining a clear transparent image.

FIG. 8 illustrates a case in which the collimator C is placed away from the X-ray source 3. It is compared how an X-ray generated at one end of the X-ray occurrence range and an X-ray generated at the other end thereof transmit through the collimator and will be projected on a projection plane. It is understood that the path along which the X-ray generated at one end of the X-ray generation range goes toward the projection plane and the path along which the X-ray generated at the other end of the X-ray generation range goes toward the projection plane are not greatly different from each other.

In the case of FIG. 8, it can be seen that the gray zone indicated by the reference symbol "d" in FIG. 7 is considerably small. As will be understood, it is desirable that the gray zone be smaller for obtaining a clear transparent image. In the case of the present invention, the phase grating 5 is farther from the X-ray source 3 than the multi-slit S. Therefore, a clear transparent image can be obtained by providing the collimator C to the phase grating 5 as in this modified example.

The present invention can also be realized by integrating the phase grating 5 and the collimator C. That is, according to the present invention, it is configured such that the collimator C and the phase grating 5 are integrated. Therefore, when the collimator C of the present invention is moved, the phase grating 5 is also moved accordingly.

According to a conventional common general technical knowledge, it is configured such that the phase grating 5 of a conventional configuration is fixed in a device. This is because the need to move the phase grating 5 was not found. The inventors of the present invention have conceived a configuration to integrate the collimator C and the phase grating 5. According to the configuration of the present invention, the device configuration becomes much simpler than a structure in which a collimator C is provided to the device independently of the phase grating 5. On the other hand, even if it is configured such that the phase grating 5 is moved, there is no problem in the image capturing. Since the phase grating 5 is configured by repeatedly arranging the same pattern, there is no problem even if scanning image capturing is performed by using the same portion of the phase grating 5.

Figure 9:
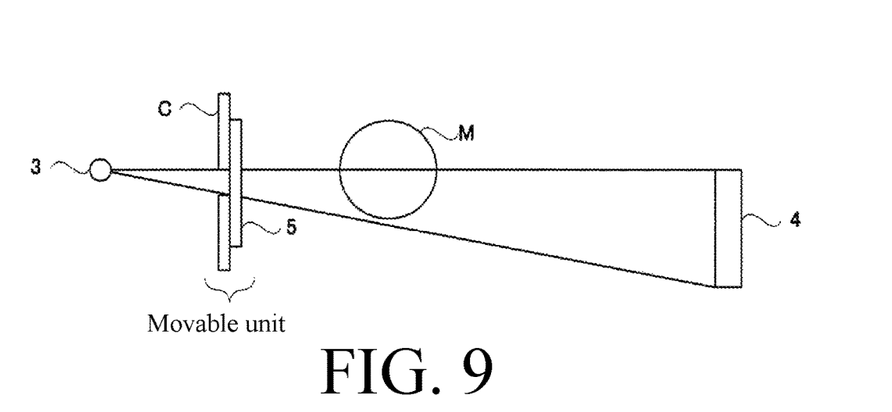
FIG. 9 is a schematic diagram illustrating the positional relationship of each of parts configuring the device according to a modified example of the present invention.

(2) As a variation of a modified example in which the collimator C is provided on the phase grating 5, a configuration in which the multi-slit S is omitted as shown in FIG. 9 can be exemplified. In some X-ray sources 3, there is an X-ray source that can output an X-ray high in coherent alone without using a multi-slit S. Such an X-ray source 3 is configured such that diamond films are arranged at equal intervals in the X-ray generation range described in FIGS. 7 and 8, and is configured to generate a stripe-like X-ray beam.

A stripe-shaped X-ray beam interferes as it spreads and becomes a phase-aligned X-ray beam. Therefore, in the configuration of FIG. 9, even if a multi-slit S is omitted, the X-ray phase-contrast by Talbot interference can be imaged.

Figure 10:
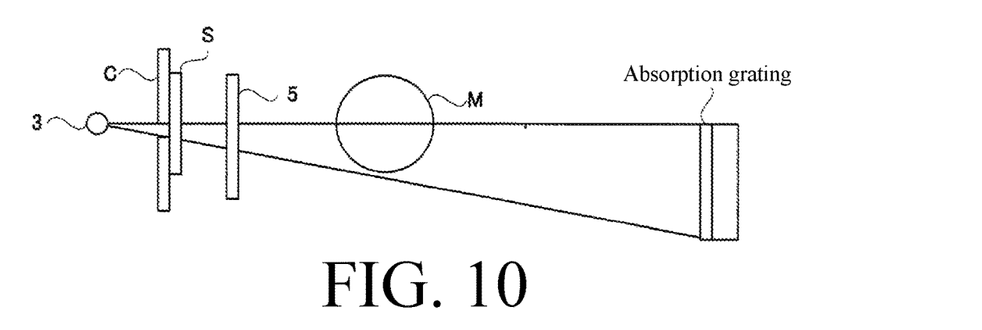
FIG. 10 is a schematic diagram illustrating the positional relationship of each of parts configuring the device according to a modified example of the present invention.

(3) According to the configuration of Example 1, nothing is provided in the detection surface of the FPD 4, but the present invention is not limited to this configuration. As shown in FIG. 10, an absorption grating may be provided so as to cover the detection surface of the FPD 4. The absorption grating is configured by elongated absorbers absorbing an X-ray arranged in a stripe manner, and is a grating which generates moire between the absorption grading and the self-image of phase grating 5. The FPD 4 detects this moire. The self-image image generation unit 11 according to the present modification can reconstruct a self-image by the analysis of the moire. In the absorption grating, an absorption grating in which absorbers absorbing an X-ray and extending in the longitudinal direction are arranged in the lateral direction is provided so as to cover the X-ray incident surface of the FPD 4.

In this case, by alternately repeating the scanning image capturing and the movement of the absorption grating, the moire image over the entire object can be image captured many times. In single scan image capturing, it is assumed that a moire image fragment reflecting moiré, for example, is image captured three times. The image capturing of these three pieces is performed with the positional relationship between the FPD 4 and the absorption grating constant. The obtained three pieces are combined by the self-image image generation unit 11, and a moire image over the entire object is generated. In this way, the $1^{st}$ scanning image capturing is completed and one moire image is generated. In the configuration of the modified example, while changing the positional relationship of the absorption grating with respect to the FPD 4, the $2^{nd}$, $3^{rd}$, and $4^{th}$ scanning image capturing are performed, and a moire image over the entire object is generated each time. The self-image image generation unit 11 generates a self-image of the phase grating 5 based on these series of moire images.

According to this modified example, even if the spatial resolution of the FPD 4 is low, the self-image of the phase grating 5 can be imaged.

Figure 11:
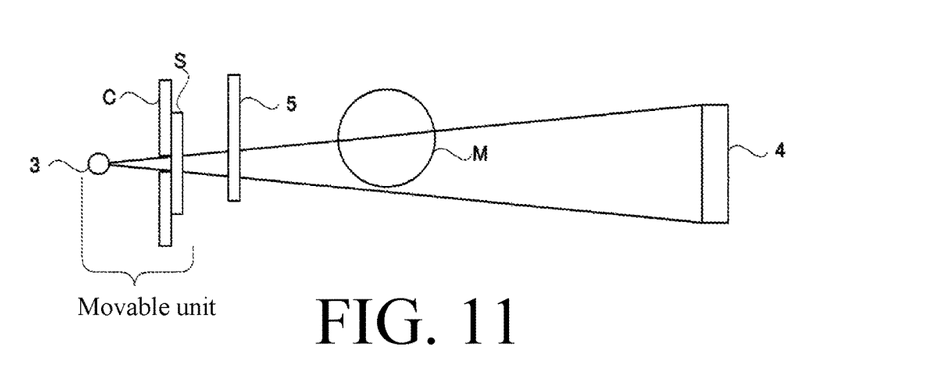
FIG. 11 is a schematic diagram illustrating the positional relationship of each of parts configuring the device according to a modified example of the present invention.

(4) According to the configuration of Example 1, the movable unit is composed of the collimator C and the multi-slit S, but the present invention is not limited to this configuration. As shown in FIG. 11, the X-ray source 3 may be moved together with the collimator C and the multi-slit S. The movable unit 3, C, S of this modified example can also be regarded as including the X-ray source 3.

Figure 12:
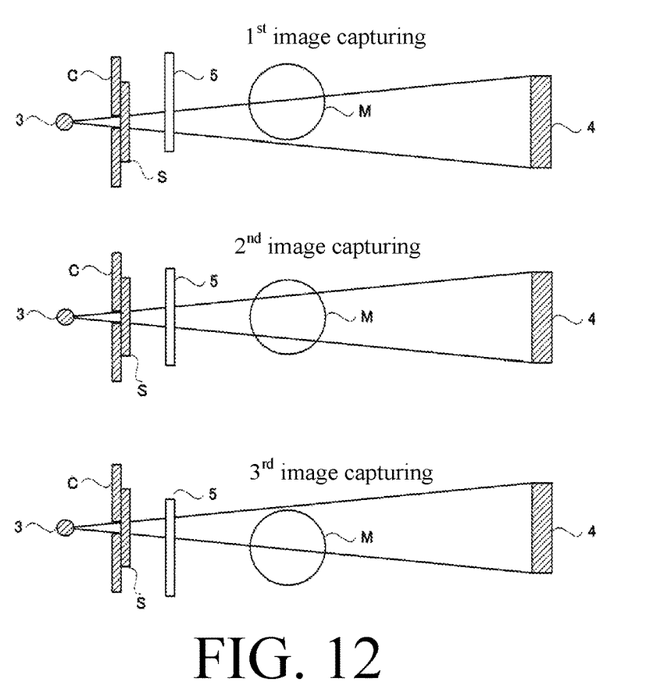
FIG. 12 is a schematic view illustrating the movement of each of parts at the time of performing the scanning image capturing according to a modified example of the present invention.

FIG. 12 illustrates the positional relationship of each of parts at the time of the scanning image capturing according to this modified example, and the movable unit 3, C, S which is composed of the X-ray source 3, the collimator C, and the multi-slit S and the FPD 4 emphasized with hatched lines moves during the scanning image capturing. At this time, each of the parts configuring the movable unit 3, C, S moves while maintaining the relative positional relationship. On the other hand, the phase grating 5 and the object M, which are not emphasized with hatched lines, do not move during the scanning image capturing.

In the configuration of Example 1, the moving speeds of the movable unit C, S and the FPD 4 during the scanning image capturing were not constant. But, in the case of the scanning image capturing according to this modified example, the movable unit 3, C, S and the FPD 4 move in the same direction at the same speed. Therefore, the movable unit 3, C, S and the FPD 4 during the scanning image capturing move with their relative positions maintained.

In the case of this modified example, as shown in the upper, middle, and lower parts in FIG. 12, there is no change in the emission direction of the X-ray beam even when the movable unit 3, C, S is moved, so that the X-ray is incident on the FPD 4 at the shortest distance. This configuration is different from the configuration of Example 1 in which image capturing is performed while biasing the direction of the X-ray beam.

Advantages of such a configuration will be described. In the case of Example 1, when capturing image fragments, there is a case in which an X-ray is diagonally applied to the multi-slit S. The multi-slit S is made of a member having a thickness so as to assuredly absorb an X-ray. Looking at such a multi-slit S from the front, as shown on the left side in FIG. 13, it seems as if there is no thickness and the through-holes are arranged in order. However, when looking at the multi-slit S from an oblique direction, the side surface of the multi-slit S becomes visible as shown on the right side in FIG. 13. Since this situation is the same also inside the through-hole, it looks that the through-hole is partially blocked. That is, when an X-ray is applied to the multi-slit S in an oblique direction, a part of X-ray passing through the through-hole is absorbed by the side surface of the multi-slit S. This phenomenon cannot happen when an X-ray is applied from the front of the multi-slit S.

Figure 13:
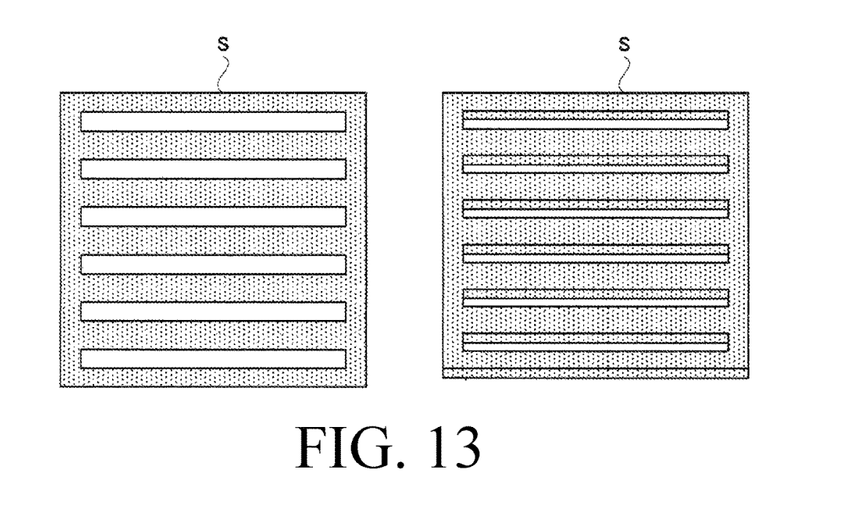
FIG. 13 is a schematic diagram illustrating advantages possessed by a modified example of the present invention.

In such circumstances, the amount of X-ray passing through the multi-slit S increases when an X-ray is irradiated to the multi-slit S in a direction perpendicular to the multi-slit S than when irradiated in a diagonal direction. In the case of this modified example, since an X-ray always is incident on the multi-slit S from an direction orthogonal to the X-ray, the image capturing of fragments can always be performed with a strong X-ray amount, and there occurs no exposure shortage when image capturing each fragment.

(5) In the aforementioned modified example (4), the movable unit is composed of the collimator C, the multi-slit S, and the X-ray source 3, but an FPD 4 may be added to this configuration. In doing so, the FPD moving mechanism 15 and the FPD movement control unit 16 shown in FIG. 1 can be omitted.

Figure 14:
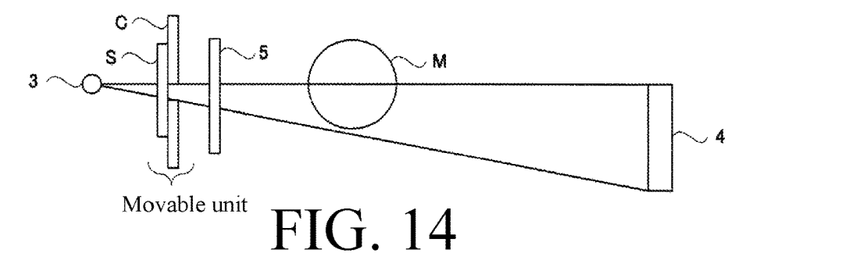
FIG. 14 is a schematic diagram illustrating the positional relationship of each of parts configuring the device according to a modified example of the present invention.

(6) In the configuration of Example 1, the collimator C is provided on the surface of the multi-slit S on the X-ray source 3 side, but the present invention is not limited to this configuration. As shown in FIG. 14, the collimator C may be provided on the surface of the multi-slit S on the FPD 4 side.

Figure 15:
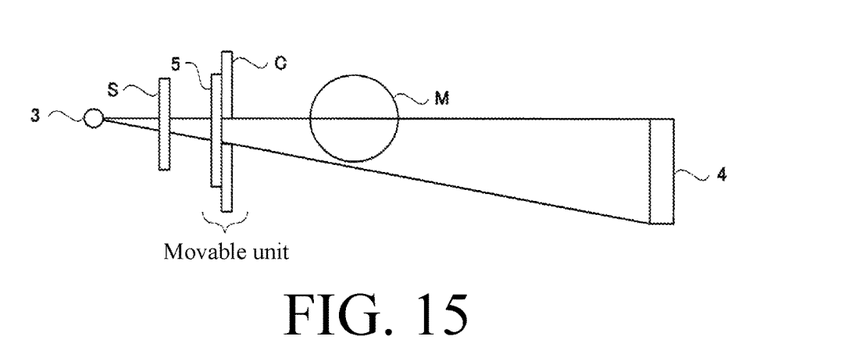
FIG. 15 is a schematic diagram illustrating the positional relationship of each of parts configuring the device according to a modified example of the present invention.

(7) In the configuration of the aforementioned modified examples (1) and (2), the collimator C is provided on the surface of the phase grating 5 on the side of the X-ray source 3, but the present invention is not limited to this configuration. As shown in FIG. 15, the collimator C may be provided on the surface of the phase grating 5 on the FPD 4 side.

Figure 16:
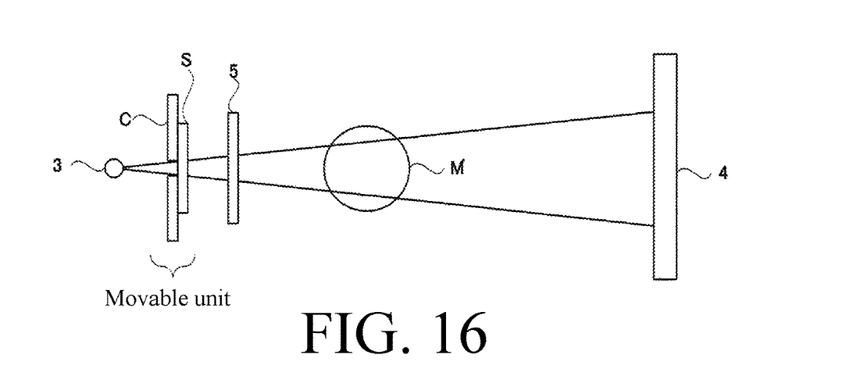
FIG. 16 is a schematic diagram illustrating the positional relationship of each of parts configuring the device according to a modified example of the present invention.

(8) In the configuration of Example 1, the FPD 4 has been made compact, but the present invention is not limited to this configuration. As shown in FIG. 16, the FPD 4 may be made large and the X-ray may be detected by a part of the FPD 4. Such a device configuration is effective when it is desired to image-capture only a part of the object M. In the configuration of this modified example, it is not always necessary to move the FPD 4, and it is not always necessary to provide the FPD moving mechanism 15 and the FPD movement control unit 16.

(9) In addition, Example 1 and modified examples according to the present invention may be combined and carried out.

DESCRIPTION OF REFERENCE SYMBOLS

C: collimator
S: multi-slit
3: X-ray source (radiation source)
4: FPD (detector)
5: phase grating
11: self-image image generation unit (image combining unit)
13: movable unit drive mechanism (unit moving mechanism)
15: FPD moving mechanism (detector moving mechanism)

The invention claimed is:

1. A radiation phase-contrast image capturing device comprising:
    a radiation source configured to irradiate radiation;
    an integrally formed multi-slit and collimator unit comprising a multi-slit integrally formed with a collimator, the multi-slit being configured to align phases of radiation generated from the radiation source and transmitted through the multi-slit and the collimator being configured to limit the spread of the radiation;
    a phase grating including a plurality of absorbers configured to absorb radiation and extending in a longitudinal direction, the plurality of absorbers being arranged side by side in a lateral direction, the phase grating being configured to cause the occurrence of Talbot interference when radiation is transmitted therethrough;
    a detector configured to detect a self-image of the phase grating, wherein the radiation source, the unit, the phase grating, and the detector are arranged in this order; and
    a unit moving mechanism configured to move the multi-slit and the collimator together in a direction orthogonal to an irradiation direction of the radiation at the unit to change a position where radiation collimated with the unit is incident on an object positioned between the unit and the detector.

2. The radiation phase-contrast image capturing device as recited in claim 1, wherein
    the radiation source is integrated with the unit, and
    the unit moving mechanism is configured to move the multi-slit, the collimator, and the radiation source together.

3. A radiation phase-contrast image capturing device comprising:
    a radiation source configured to irradiate radiation;
    a unit comprising a phase grating integrally formed with a collimator, the phase grating including a plurality of absorbers configured to absorb radiation and extending in a longitudinal direction, the plurality of absorbers being arranged side by side in a lateral direction, the phase grating being configured to cause the occurrence of Talbot interference when radiation is transmitted therethrough and the collimator being configured to limit the spread of the radiation;
    a detector configured to detect a self-image of the phase grating, wherein the radiation source, the unit, and the detector are arranged in this order; and
    a unit moving mechanism configured to move the phase grating and collimator together in a direction orthogonal to an irradiation direction of the radiation at the unit to change a position where radiation collimated with the unit is incident on an object positioned between the unit and the detector.

4. The radiation phase-contrast image capturing device as recited in claim 3, further comprising:
    a multi-slit configured to align phases of radiation generated from the radiation source, the multi-slit being arranged between the radiation source and the unit.

5. The radiation phase-contrast image capturing device as recited in claim 1, wherein the detector has an elongated shape and wherein the radiation phase-contrast image capturing device further comprises:
    a detector moving mechanism configured to move the detector in a direction orthogonal to an irradiation direction of radiation at the detector in synchronization with a movement of the unit; and
    an image combining unit configured to combine a plurality of images obtained by continuous image capturing while moving the unit and the detector to generate a single image,
    wherein the unit moving mechanism and the detector moving mechanism are configured to move the unit synchronously with the detector so that the collimator transmits X-rays incident on the detector and other X-rays are absorbed in case of each shot of the plurality of images.

6. The radiation phase-contrast image capturing device as recited in claim 1, further comprising:
    an absorption grating covering a radiation incident surface of the detector, the absorption grating including a plurality of absorbers configure to absorb radiation, the plurality of absorbers extending in a longitudinal direction arranged side by side in a lateral direction.

7. The radiation phase-contrast image capturing device as recited in claim 1, further comprising:
    a control unit configured to control movement of the unit and the detector to obtain a plurality of images of an object positioned between the unit and the detector, and configured to obtain a single image by combining the plurality of images, the plurality of images including at least a first image, a second image and a third image,
    wherein the control unit is configured to obtain the first image with the unit positioned at a first unit position and the detector positioned at a first detector position,
    wherein the control unit is configured to obtain the second image with the unit positioned at a second unit position and the detector positioned at a second detector position,
    wherein the control unit is configured to obtain the third image with the unit positioned at a third unit position and the detector positioned at a third detector position, and
    wherein the first unit position, the second unit position and the third unit position are different from each other and the first detector position, the second detector position and the third detector position are different from each other.

8. The radiation phase-contrast image capturing device as recited in claim 7, wherein the control unit is configured to obtain each of the first image, the second image and the third image with the phase grating located at the same position.

9. The radiation phase-contrast image capturing device as recited in claim 7, wherein the first unit position, the second unit position and the third unit position are aligned with each other in a first direction and the first detector position, the second detector position and the third detector position are aligned with each other in the first direction.

10. The radiation phase-contrast image capturing device as recited in claim 1, further comprising:
    a control unit configured to control movement of the unit and the detector and to obtain a single combined image from a plurality of images of an object that are taken with different relative positioning between the unit and the phase grating.

11. The radiation phase-contrast image capturing device as recited in claim 10,
wherein the unit moving mechanism is configured to move the multi-slit and collimator together to a first unit position, a second unit position and a third unit position, and
wherein the plurality of images includes at least a first image, a second image and a third image,
wherein the control unit is configured to obtain the first image, the second image and the third image with the phase grating at the same position and with the multi-slit and collimator unit respectively at the first unit position, the second unit position and the third unit position.

12. The radiation phase-contrast image capturing device as recited in claim 10,
wherein the plurality of images comprise at least a first image, a second image and a third image,
wherein the control unit is configured to obtain the first image, the second image and the third image respectively at a first unit position, a second unit position and a third unit position of the unit, and
wherein the collimator comprises a window that exposes the same portion of the multi-slit at the first unit position, the second unit position and the third unit position and exposes different portions of the phase grating at the first unit position, the second unit position and the third unit position.

13. The radiation phase-contrast image capturing device as recited in claim 1, wherein the multi-slit and the collimator are adhered together.

14. The radiation phase-contrast image capturing device as recited in claim 3, further comprising:
a control unit configured to control movement of the unit and the detector to obtain a plurality of images of an object positioned between the unit and the detector, and configured to obtain a single image by combining the plurality of images, the plurality of images including at least a first image, a second image and a third image,
wherein the control unit is configured to obtain the first image with the unit positioned at a first unit position and the detector positioned at a first detector position,
wherein the control unit is configured to obtain the second image with the unit positioned at a second unit position and the detector positioned at a second detector position,
wherein the control unit is configured to obtain the third image with the unit positioned at a third unit position and the detector positioned at a third detector position, and
wherein the first unit position, the second unit position and the third unit position are different from each other and the first detector position, the second detector position and the third detector position are different from each other.

15. The radiation phase-contrast image capturing device as recited in claim 14, wherein the first unit position, the second unit position and the third unit position are aligned with each other in a first direction and the first detector position, the second detector position and the third detector position are aligned with each other in the first direction.

16. The radiation phase-contrast image capturing device as recited in claim 3, further comprising:
a control unit configured to control movement of the unit and the detector and to obtain a single combined image from a plurality of images of an object that are taken with different relative positioning between the unit and the radiation source.

17. The radiation phase-contrast image capturing device as recited in claim 16,
wherein the unit moving mechanism is configured to move the unit to a first unit position, a second unit position and a third unit position, and
wherein the plurality of images includes at least a first image, a second image and a third image,
wherein the control unit is configured to obtain the first image, the second image and the third image with the radiation source at the same position and with the unit respectively at the first unit position, the second unit position and the third unit position.

18. The radiation phase-contrast image capturing device as recited in claim 16,
wherein the plurality of images comprise at least a first image, a second image and a third image,
wherein the control unit is configured to obtain the first image, the second image and the third image respectively at a first unit position, a second unit position and a third unit position of the unit, and
wherein the collimator comprises a window that exposes the same portion of the phase grating at the first unit position, the second unit position and the third unit position.

19. The radiation phase-contrast image capturing device as recited in claim 18, further comprising a multi-slit interposed between the radiation source and the unit through which radiation of the radiation source passes to impinge on the phase grating,
wherein the same portion of the phase grating exposed by the window of the collimator is positioned to receive radiation from different portions of the multi-slit when the phase grating is at the first unit position, the second unit position and the third unit position.

20. The radiation phase-contrast image capturing device as recited in claim 3, wherein the detector has an elongated shape and wherein the radiation phase-contrast image capturing device further comprises:
a detector moving mechanism configured to move the detector in a direction orthogonal to an irradiation direction of radiation at the detector in synchronization with a movement of the unit; and
an image combining unit configured to combine a plurality of images obtained by continuous image capturing while moving the unit and the detector to generate a single image,
wherein the unit moving mechanism and the detector moving mechanism are configured to move the unit synchronously with the detector so that the collimator transmits X-rays incident on the detector and other X-rays are absorbed in case of each shot of the plurality of images.

* * * * *